US00PP19982P2

(12) United States Plant Patent
Klemm

(10) Patent No.: US PP19,982 P2
(45) Date of Patent: May 12, 2009

(54) *DIASCIA* PLANT NAMED 'KLEDB07513'

(50) Latin Name: *Diascia hybrida*
Varietal Denomination: KLEDB07513

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/079,986

(22) Filed: Mar. 31, 2008

(51) Int. Cl.
*A01H 5/00* (2006.01)

(52) U.S. Cl. ..... Plt./425

(58) Field of Classification Search ..... Plt./425
See application file for complete search history.

*Primary Examiner*—Annette H Para
(74) *Attorney, Agent, or Firm*—Jondle & Associates, P.C.

(57) ABSTRACT

A new *Diascia* plant particularly distinguished by having large, intense hot pink flowers and a rounded, semi-trailing, medium-compact growth habit, is disclosed.

1 Drawing Sheet

Genus and species: *Diascia hybrida.*
Variety denomination: 'KLEDB07513'.

BACKGROUND OF THE NEW PLANT

The present invention comprises a new and distinct cultivar of *Diascia* , botanically known as *Diascia hybrida,* and hereinafter referred to by the cultivar name 'KLEDB07513'. The new cultivar originated from a hybridization made in June 2004 in Stuttgart, Germany. The female parent was the *Diascia* plant 'KLEDI04016' (U.S. Plant Pat. No. 17,857), while the male parent was the proprietary *Diascia* plant 'KLED104018' (U.S. Plant Pat. No. 18,069).

The new cultivar was first propagated in 2005 in Stuttgart, Germany and has been asexually reproduced by vegetative cuttings and in-vitro propagation in Stuttgart, Germany over a two-and-one-half year period. The present invention has been found to retain its distinctive characteristics through successive asexual propagations.

Plant Breeder's Rights for this cultivar were applied for in Canada on Mar. 28, 2007. 'KLEDB07513' has not been made publicly available more than one year prior to filing of this application.

SUMMARY OF THE INVENTION

The following are the most outstanding and distinguishing characteristics of this new cultivar when grown under normal horticultural practices in a greenhouse in Stuttgart, Germany.

1. Large, intense hot pink flowers; and
2. A round, semi-trailing, medium-compact growth habit.

DESCRIPTION OF PHOTOGRAPH

This new *Diascia* plant is illustrated by the accompanying photograph which shows overall plant habit including blooms, buds, and foliage of the plant; the colors shown are as true as can be reasonably obtained by conventional photographic procedures. The photograph is of a plant six-and-one-half months old, grown in a field in Stuttgart, Germany, in August 2007.

DESCRIPTION OF THE NEW CULTIVAR

The following detailed descriptions set forth the distinctive characteristics of 'KLEDB07513'. The data which defines these characteristics were collected from asexual reproductions carried out in Stuttgart, Germany. The plant history was taken on six-and-one-half month old plants which were planted as rooted cuttings in 10-cm pots in August 2007, and then grown in a field. The plants had one pinch two weeks after sticking. Color readings were taken under natural light in the field. Color reference are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Scrophulariaceae.
- *Botanical name.*—*Diascia hybrida.*
- *Common name.*—*Diascia.*

Parentage:
- *Female.*—*Diascia* plant 'KLEDI04016' (U.S. Plant Pat. No. 17,857), having pink flowers.
- *Male.*—*Diascia* plant 'KLEDI04018' (U.S. Plant Pat. No. 18,069), having red flowers.

Growth:
- *Form and growth habit.*—Rounded, semi-trailing, medium compact.
- *Height.*—17 cm to 25 cm.
- *Width.*—40 cm (excluding flowers and inflorescence).
- *Spread (including flowers).*—50 cm.
- *Time to produce a finished flowering plant.*—Ten weeks after sticking.
- *Outdoor plant performance.*—Good tolerance to wind and rain.
- *Time to initiate and develop root.*—10 to 14 days.
- *Root description.*—Fibrous, white and dense.

Leaves:
- *Arrangement.*—Opposite.
- *Shape.*—Ovate.
- *Apex.*—Obtuse.
- *Base.*—Truncate.
- *Margin.*—Serrate.

*Immature.*—Color: Upper surface: RHS 143A. Lower surface: RHS 143D. Texture: Leathery.

*Mature* (*fully expanded*).—Length: 1 cm to 2 cm. Width: 0.5 cm to 1.5 cm. Color: Upper surface: RHS 143A. Lower surface: RHS 143D.

*Venation.*—Type: Palmate. Color: RHS 146B.

*Texture* (*both surfaces*).—Leathery.

*Petiole.*—Length: 0.1 cm to 0.5 cm. Width: 0.1 cm. Color: RHS 146B.

Stems:

*Length.*—20 cm.

*Diameter.*—0.1 cm to 0.2 cm.

*Color.*—RHS 144A.

*Texture.*—Smooth, glabrous.

*Anthocyanin.*—Absent.

Flower Bud:

*Shape.*—Round.

*Diameter.*—0.2 cm to 0.4 cm.

*Length.*—0.1 cm to 0.2 cm.

*Color* (*at tight bud*).—RHS 73D at the tip, RHS 155D at the base.

Inflorescence:

*Inflorescence type.*—Raceme.

*Blooming habit.*—Continuous.

*Quantity of inflorescences per plant.*—10 to 40.

*Lastingness of individual blooms on the plant.*—5 days.

*Fragrance.*—Absent.

*Size.*—Height: 5.0 cm to 10.0 cm. Width: 3.0 cm.

*Peduncle.*—Color: RHS 144B. Length: 5 cm. Diameter: 0.1 cm. Texture: Leathery, smooth, glabrous.

Flower:

*Type.*—Solitary-zygomorphic flowers arranged on terminal racemes.

*Quantity* (*per raceme*).—5.

*Shape.*—5 modified petals fused at base.

*Length.*—1.5 cm.

*Depth.*—0.5 cm.

*Width.*—1.2 cm.

*Color.*—Upper surface: RHS 59D. Lower surface: RHS 59D. Corolla (inside color): RHS 59D.

*Petals* (*lobes*): Quantity: 5. Arrangement: Modified petals fused at base. Apex: Obtuse. Base: Open, fused into a tube. Margin: Entire. Texture (both surfaces): Leathery.

*Upper lobes, size.*—Length (from the corolla opening): 0.5 cm to 1.0 cm. Width: 1.0 cm to 1.5 cm.

*Lateral lobes, size.*—Length (from the corolla opening): 0.5 cm to 1.0 cm. Width: 1.0 cm to 1.5 cm. Spur: Number: 2. Aspect: Downward curving; degree of curvature is medium. Length: 0.5 cm. Diameter: 0.1 cm. Color: RHS 64C, with RHS 83A (Violet) at the tip.

*Lower lobe.*—Length (from the corolla opening): 0.5 cm to 1.0 cm. Width: 1.0 cm to 1.5 cm.

*Sepals.*—Quantity: 5. Color: Upper surface: RHS 146B. Lower surface: RHS 146D. Length: 0.2 cm. Width: 0.1 cm. Shape: Oblong. Apex: Acute. Base: Fused. Anthocyanin: Absent. Texture (both surfaces): Leathery.

*Pedicels.*—Color RHS 144B. Length: 0.8 cm to 1.3 cm. Diameter: 0.1 cm. Texture: Smooth, glabrous.

Reproductive Organs:

*Stamens.*—Quantity: 4. Filament: Color: RHS 77A. Length: 0.3 cm. Diameter 0.1 cm. Anther color: RHS 15B. Pollen color: RHS 15B.

*Pistils.*—Quantity: 1. Length: 0.2 cm to 0.3 cm. Stigma color: RHS 142B. Style color: RHS 144B.

Fruit and Seed Set: No seed set observed.

Disease and insect resistance: No particular resistance or susceptibility has been observed.

COMPARISON WITH PARENTAL AND COMMERCIAL CULTIVARS

'KLEDB07513' differs from the female parent 'KLED104016' (U.S. Plant Pat. No. 17,857) by having hot pink flowers with a medium-compact growth habit, while 'KLEDI04016' has pink flowers and a growth habit that is not compact.

'KLEDB07513' differs from the male parent 'KLED104018' (U.S. Plant Pat. No. 18,069), by having large, hot pink flowers, while 'KLEDI04018' has smaller, light-red flowers.

'KLEDB07513' differs from the commercial cultivar 'Picadilly Hot Pink' (unpatented) by having larger flowers with a more intense pink flower color than 'Picadilly Hot Pink'. Additionally, 'KLEDB07513' has a more compact growth habit than 'Picadilly Hot Pink'.

I claim:

1. A new and distinct cultivar of *Diascia* plant as shown and described herein.

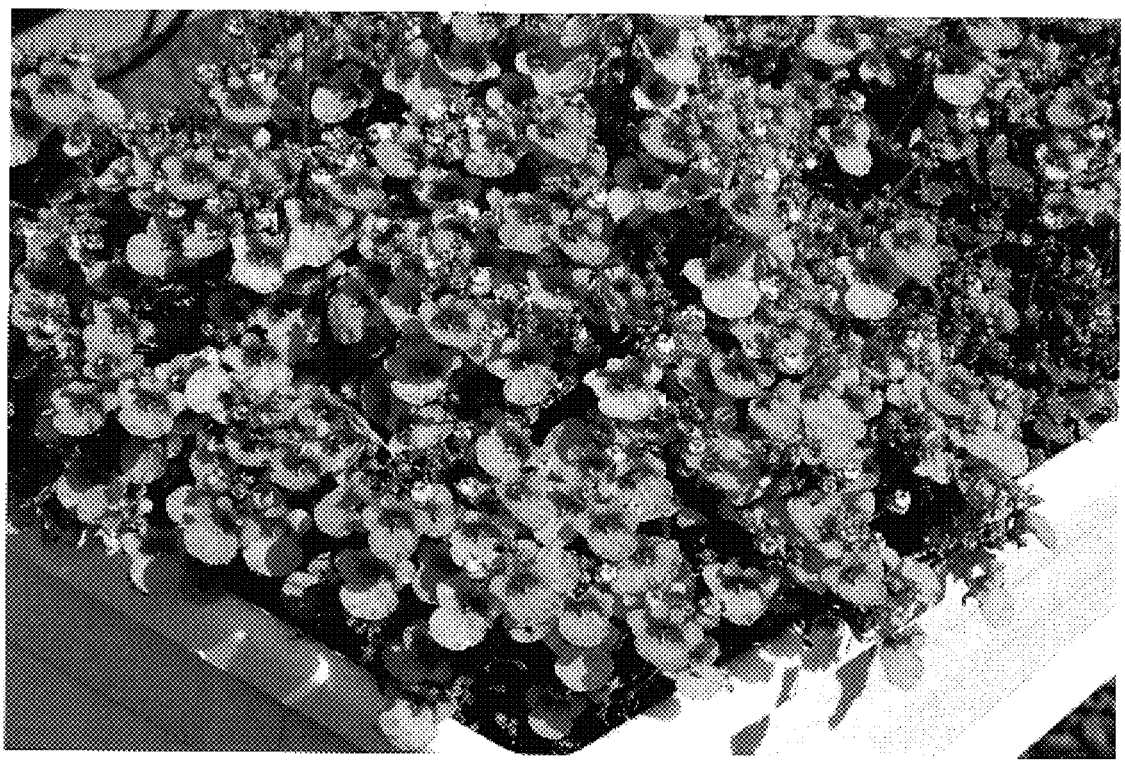

* * * * *